United States Patent
Henning et al.

(12) 
(10) Patent No.: US 6,565,738 B1
(45) Date of Patent: May 20, 2003

(54) DIAGNOSTIC TEST FOR THE MEASUREMENT OF ANALYTE IN ABIOLOGICAL FLUID

(75) Inventors: Timothy P. Henning, Vernon Hills, IL (US); Kristen L. Cousineau, Lindenhurst, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/239,200

(22) Filed: Jan. 28, 1999

(51) Int. Cl.[7] .............................................. G01N 27/327
(52) U.S. Cl. .............................. 205/777.5; 204/403.01; 204/403.14
(58) Field of Search .......................... 204/403, 403.01, 204/403.14; 435/817; 205/777.5

(56) References Cited

U.S. PATENT DOCUMENTS

| | | | | |
|---|---|---|---|---|
| 4,240,889 A | * | 12/1980 | Yoda et al. | 204/403 |
| 4,450,232 A | | 5/1984 | Sanford et al. | 435/15 |
| 4,575,488 A | | 3/1986 | Krouwer et al. | 435/16 |
| 4,713,165 A | * | 12/1987 | Conover et al. | 204/403 |
| 4,897,173 A | | 1/1990 | Nankai et al. | 204/403 |
| 4,897,347 A | | 1/1990 | Katsuyama et al. | 435/16 |
| 5,131,999 A | * | 7/1992 | Gunasingham | 204/411 |
| 5,171,689 A | * | 12/1992 | Kawaguri et al. | 204/403 |
| 5,288,636 A | | 2/1994 | Pollmann et al. | 435/288 |
| 5,320,732 A | * | 6/1994 | Nankai et al. | 204/403 |
| 5,462,858 A | | 10/1995 | Bale Oenick et al. | 435/6 |
| 5,520,787 A | * | 5/1996 | Hanagan et al. | 204/409 |

(List continued on next page.)

FOREIGN PATENT DOCUMENTS

| | | |
|---|---|---|
| DE | 247-285 A | 7/1987 |
| DE | 248-605 A | 8/1987 |
| EP | 0 136 362 | 4/1985 |
| GB | 2 161 274 | 1/1986 |
| JP | 60095-344 A | 5/1985 |
| JP | 61081-799 A | 4/1986 |
| WO | 98/20331 | 5/1998 |
| WO | 98/24366 | 6/1998 |

OTHER PUBLICATIONS

Cooper, et al., "Amperometric enzyme electrode for the determination of aspartate aminotransferase and alanine aminotransferase in serum", Analytica Chimica Acta, 245 (1991) 57–62.

*Primary Examiner*—T. Tung
*Assistant Examiner*—Alex Noguerola
(74) *Attorney, Agent, or Firm*—David L. Weinstein

(57) ABSTRACT

A biosensor for determining the concentration of an analyte, such as, for example, ALT, in a sample of biological fluid, such as, for example, whole blood, comprising:

(a) a base layer;
(b) a detecting layer comprising a reference electrode and a working electrode, the surface of the electrically conductive portion of the working electrode being sufficiently smooth so that determination of the concentration of an analyte present in a low concentration, e.g., less than 1 mM, can be made;
(c) a layer overlying said electrodes, said layer comprising dried reagents; and
(d) an anticoagulant disposed in such a location that it will prevent the sample from coagulating during the determination.

The biosensor preferably further includes a fluid-transporting layer to aid in delivering the sample from a sample application zone to the electrodes. The biosensor preferably further includes a covering layer overlying the electrode area to reduce evaporation of the sample during the assay and to help define the fluid transport path and the volume of fluid over the detecting layer.

16 Claims, 9 Drawing Sheets

U.S. PATENT DOCUMENTS

| | | |
|---|---|---|
| 5,628,890 A | 5/1997 | Carter et al. .................. 204/403 |
| 5,658,444 A * | 8/1997 | Black et al. .................. 204/415 |
| 5,682,884 A | 11/1997 | Hill et al. .................... 128/657 |
| 5,705,045 A | 1/1998 | Park et al. ................... 206/403 |
| 5,755,953 A | 5/1998 | Henning et al. ............. 205/778 |
| 5,972,199 A * | 10/1999 | Heller et al. ............. 205/777.5 |
| 6,117,289 A * | 9/2000 | Yamamoto et al. ......... 204/403 |

\* cited by examiner

DIAGNOSTIC TEST FOR THE MEASUREMENT OF ANALYTE IN A BIOLOGICAL FLUID

BACKGROUND OF THE INVENTION

1. Field of the Invention

This invention relates to a biosensor for the determination of the concentration of an analyte in a biological fluid, such as, for example, a biosensor for the determination of alanine aminotransferase activity in whole blood.

2. Discussion of the Art

Alanine aminotransferase (hereinafter "ALT") is an enzyme that is found primarily in the liver and is released into the blood when the liver is damaged. ALT is an important analyte, the concentration of which is elevated in almost all disorders of the liver. ALT measurement is used to help diagnose liver disorders or liver damage, such as from hepatitis, toxins, or adverse reactions to ethical drugs. The number of estimated deaths in the United States in 1994 attributed to adverse drug reactions was over 100,000, making adverse drug reaction the fifth leading cause of death in the United States. The estimated cost of adverse drug reactions in the United States is over 77 billion dollars per year. A single ALT measurement does not indicate whether the liver damage is progressing. Consequently, serial ALT measurements are frequently used to aid in the diagnosis of a liver disorder and to follow its progress.

ALT assays of the prior art have typically employed blood collected from an individual through a needle in the arm connected to an evacuated tube and processed by centrifugation to acquire serum or plasma. The serum or plasma is then evaluated for ALT activity by a trained operator, usually by means of a test system employing an instrument that is normally at least as large as a personal computer. The reagents used in these ALT assays generally exhibit limited stability at ambient and elevated temperatures. Therefore, the reagents must typically be stored at a location removed from the instrument and under refrigerated conditions. Assays that employ liquid reagents typically require precise addition of the reagents to the serum or plasma and mixing the added reagents with the serum or plasma to obtain accurate ALT measurements.

Because of the complexity of ALT assays currently available, trained operators must conduct the assays. Moreover, the large size of the analyzers prohibit system portability. For these reasons, the patient must travel to a patient-care facility to have an ALT assay run. Some patients must have their ALT levels monitored regularly by their physician for months, or even years.

The field of self-monitoring is well established in the area of diabetes. Self-monitoring devices for determining blood glucose levels have been available to patients since the mid 1980's. These devices use a fingerstick to obtain whole blood and are very simple to operate. It would be desirable to develop an ALT assay that is simple enough for patients to run by themselves without the need to travel to a patient-care facility U.S. Pat. No. 5,705,045 describes a biosensor capable of measuring both ALT and aspartate aminotransferase (AST) simultaneously. The biosensor contains two sets of electrodes, each set being sensitive to a different liver enzyme. Each electrode consists of a screen-printed layer containing carbon, enzyme, and binder. Overlying this layer is a screen-printed layer containing reagents and binder. In an assay employing this biosensor, a biological fluid containing ALT or AST is placed on the biosensor. The ALT or AST reacts with the reagents to produce peroxide or NADH, which is then oxidized, thereby resulting in a current that is proportional to the concentration of whichever liver enzyme is being measured. The patent describes two different chemical reactions for measuring liver enzymes. One chemical reaction produces peroxide and the other produces NADH. Any system that uses NADH to detect ALT requires NAD, which is expensive and unstable. A system that uses peroxide to detect ALT does not need NAD and would therefore be less expensive and more stable. The sensor has a cover that forms a capillary zone to move a sample from a sample application zone to the electrodes. The sensor has reagents mixed into the binder. The reagents and the binder dissolve upon exposure to the sample. In such systems, the analyte measurement must be carried out immediately after exposure of the electrode to the sample because the product of the chemical reaction and carbon diffuse away from the surface of the electrode, resulting in greatly reduced signals at long reaction times. ALT concentrations in humans are very low. The ALT reaction pathway in U.S. Pat. No. 5,705,045 requires a reaction time of several minutes to produce a measurable amount of $H_2O_2$. Therefore, this method of ALT measurement will not operate with a soluble binder system.

There is no mention of whole blood as a suitable sample in U.S. Pat. No. 5,705,045. If whole blood were to be used as a sample, the sample would clot over the sensor during the reaction period. A whole blood sample would have to be treated with an anticoagulant at a location remote from the biosensor. Capillary blood from a fingerstick could not be used because there is no means to easily add an anticoagulant to it. This deficiency would prevent the sensor from being used for home testing because capillary blood is the only sample accessible to the patient.

The measurement of ALT and AST by a biosensor was also described by Cooper et al., in Analytica Chimica Acta, 245 (1991) 57–62. Cooper employs an electrode made from platinized carbon. The sample of serum is diluted with a liquid reagent prior to the determination. Liquid reagents are undesirable because they require mixing with the sample prior to initiation of the assay. Liquid reagents are also typically less stable than dry reagents. Adding liquid reagent to a sample also dilutes the sample, which results in a lower ALT concentration in the sample, which is more difficult to measure than is a higher concentration of ALT in an undiluted sample. The addition of the liquid reagent to the sample must be carried out in a quantitative manner to obtain an accurate result. The system is complex and, therefore, would not be suitable for home use.

Currently, there is no ALT assay available for patients that they can carry out themselves. For existing ALT assays, there are many time-consuming and manual steps required before a result can be reported. Usually the patient must travel to a physician's office, hospital, or patient-care facility to have the assay run. Many ALT assays require serum as the sample, so a person trained in drawing blood is needed to obtain the sample from the patient by means of an unpleasant venipuncture procedure. Then, the blood sample must be processed by centrifugation to obtain the serum or plasma sample. Many ALT assays use liquid reagents, which must be stored under refrigerated conditions. When the assay is to be run, the liquid reagents must be added to the test system. Because of the complexity of the assay or test system, a trained operator is usually required. Furthermore, the concentration of ALT in blood is low, with the result that an accurate determination of ALT concentration is difficult.

SUMMARY OF THE INVENTION

This invention provides a biosensor for determining the concentration of an analyte, such as, for example, ALT, in a sample of biological fluid, such as, for example, whole blood, comprising:

(a) a base layer;

(b) a detecting layer comprising a reference electrode and a working electrode, the surface of the electrically conductive portion of the working electrode being sufficiently smooth so that determination of the concentration of an analyte present in a low concentration, e.g., less than 1 mM, can be made;

(c) a layer overlying said electrodes, said layer comprising dried reagents; and (d) an anticoagulant disposed in such a location that it will prevent the sample from coagulating during the determination.

The base layer provides mechanical support for all the other layers in the biosensor. The detecting layer enables a parameter of the product released by the chemical reaction of the analyte, e.g., ALT, to be transformed into a measurable current. The detecting layer comprises a reference electrode and a working electrode. The working electrode must have an electrically conductive surface of sufficient smoothness so that determination of the concentration of an analyte present in a low concentration, e.g., less than 1 mM, can be made. Such electrodes can be made of materials including, but not limited to, (1) pure metal by itself; (2) pure metal or carbon, and having a redox polymer coated on the surface thereof; (3) carbon containing an enzyme. The reagent layer provides the chemicals needed to react with the analyte in the biological fluid, e.g., ALT in blood, and produce a product that can be measured at the detecting layer. Reagents for reaction with ALT and the chemical reactions for the determination of ALT are described in detail in U.S. Pat. No. 5,705,045. The anticoagulant prevents the sample of biological fluid, e.g., a blood sample, from coagulating prior to and during the determination.

In biosensors that utilize samples of whole blood, such as those biosensors for monitoring glucose, the required chemical reaction is usually carried out in a short amount of time, usually under one minute; consequently, an anticoagulant is not required. Because the concentration of ALT in blood is low, a reaction time of several minutes is required to generate a measurable signal. Because blood begins to coagulate in approximately one minute, an anticoagulant must be added to the blood sample in order to carry out an assay for ALT. In the biosensor of this invention, an anticoagulant is contained within the biosensor and is mixed with the blood when the blood sample flows into the biosensor.

The biosensor preferably further includes a fluid-transporting layer to aid in delivering the sample from a sample application zone to the electrodes. The fluid-transporting layer moves the sample uniformly over the electrodes, and allows for the sample to wet the surfaces of the electrodes sufficiently. The fluid-transporting layer may comprise a surfactant coated mesh material and may further contain one or more reagents for the ALT assay and an anticoagulant.

The biosensor preferably further includes a covering layer overlying the electrode area to reduce evaporation of the sample during the assay and to help define the fluid transport path and the volume of fluid over the detecting layer. The covering layer is highly desirable for the ALT assay because the ALT assay requires a relatively long reaction time.

The biosensor is of sufficient size that it can be picked up and inserted into a monitoring device by untrained operators, who are frequently infirm and have limited dexterity.

The biosensor may further include a redox polymer coated on the surface of the working electrode, wherein an enzyme, such as peroxidase, is covalently linked to a redox polymer. Electrodes employing such redox polymers have high sensitivity and can be run at low operating potentials (0 to 100 mV), thereby reducing the system's sensitivity to electrochemical interferants. The detecting layer may further include an enzyme incorporated into the working electrode, as described in U.S. Pat. No. 5,755,953. Electrodes employing such incorporated enzymes have high sensitivity and can be run at low operating potentials (0 to 100 mV), thereby reducing the sensitivity of the system to electrochemical interferants.

This invention provides several advantages. The ALT assay is sufficiently simple that the patient can run it himself. Pre-treatment of sample is not required because the biosensor contains an anticoagulant. The steps needed to obtain a result are few. Because the ALT assay may use whole blood from a fingerstick sample, instead of a blood sample drawn by means of a syringe, the test can be run outside of patient-care setting, such as at home by the patient. The ALT assay typically requires sample volumes ranging from about 3.5 $\mu$L to about 20 $\mu$L, which amounts can easily be obtained from a fingerstick sample. The system is portable. Additionally, the result can be reported within minutes. Another advantage of the invention is that the biosensor employs dried reagents, thereby providing longer storage stability than assays requiring liquid reagents. Additionally, the biosensor does not require storage under refrigerated conditions.

The biosensor of this invention provides a rapid and simple ALT assay using whole blood that a patient with minimal training can run. The blood can be collected from a fingerstick in a setting where there are no trained medical professionals.

DETAILED DESCRIPTION

As used herein, the expression "electrically conductive portion" means the part of an electrode in which electrons can flow. This part is in contrast with a part of an electrode in which electrons do not flow, such as, for example, a redox polymer coating. "Redox polymer" means a polymer that can be oxidized and reduced. The redox polymer may have one or more functions that are reducible and oxidizable. Stated another way, the expression "redox polymer" means a polymer that contains one or more redox centers, "redox center" meaning a chemical function that accepts and transfers electrons.

This invention provides a biosensor for measuring ALT in a sample of whole blood. The biosensor comprises:

(a) a base layer;

(b) a detecting layer comprising a reference electrode and a working electrode, the surface of the electrically conductive portion of the working electrode being sufficiently smooth so that determination of the concentration of an analyte present in a low concentration, e.g., less than 1 mM, can be made;

(c) a layer overlying said electrodes, said layer comprising dried reagents; and (d) an anticoagulant disposed in such a location that it will prevent the sample from coagulating during the determination.

Figure 1A:
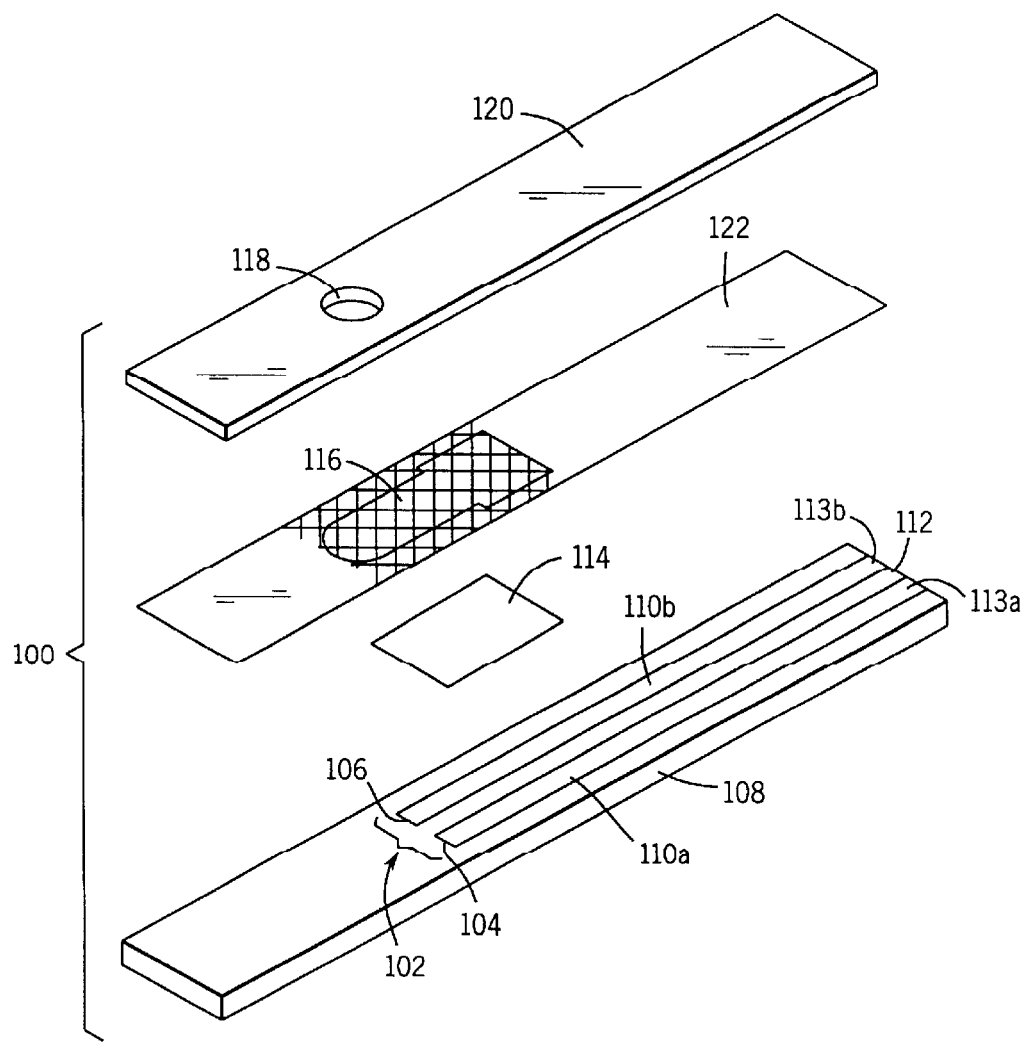
FIG. 1A is an exploded perspective view of a biosensor suitable for use in this invention.
Figure 1B:
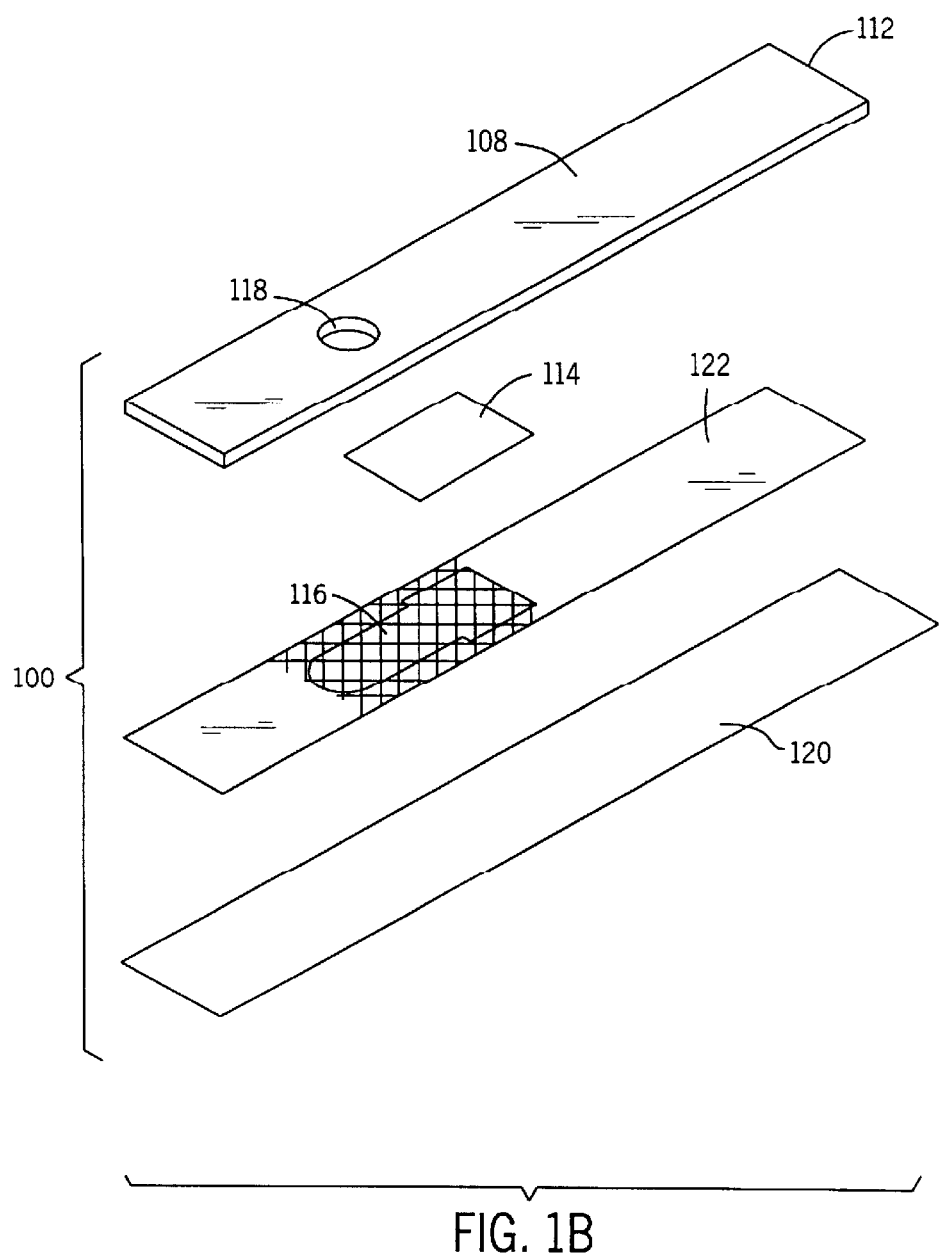
FIG. 1B is an exploded perspective view of a biosensor suitable for use in this invention.

FIGS. 1A and 1B are exploded views of biosensors suitable for use in this invention. Referring now to FIG. 1A, the biosensor, which is in the form of a multiple-layer element 100, has a detecting layer 102 comprising a working electrode 104 and a reference electrode 106. The surface of the electrically conductive portion of the working electrode 104 is sufficiently smooth so that determination of the concentration of an analyte present in a low concentration, e.g., less than 1 mM, can be made. As used herein, the surface of the working electrode is sufficiently smooth for the purposes of this invention when the arithmetic average roughness ($R_a$) does not exceed 50,000, preferably 30,000, more preferably 10,000. The electrodes are disposed on a non-conductive base layer 108. The base layer 108 supports the detecting layer 102 and all the other layers of the biosensor 100. Conductive tracks 110a and 110b from the electrodes 104, 106 to the end 112 of the non-conductive base layer 108 of the multiple-layer element 100 provide for electrical connection to a meter (not shown). The base layer 108 is also often referred to as the meter-contactable layer. The names base layer and meter-contactable layer are used interchangeably.

The detecting layer 102 can be disposed on a major surface of the meter-contactable layer 108. The detecting layer 102 comprises a first conductive track 110a and a second conductive track 110b extending along the meter-contactable layer 108 and further comprises a means for connection to circuitry that provides a display of the measurement. These means for connection are electrical contacts 113a and 113b. The electrical contacts 113a, 113b of the detecting layer 102 can be inserted into a meter, which can provide a visual display of the current generated. The working electrode 104, positioned to contact the liquid blood sample and the first conductive track 110a, comprises a pure metal or carbon capable of producing a current as a result of the reaction of ALT with reagent(s) in the reagent layer 114. The reference electrode 106 is positioned to contact the liquid blood sample and the second conductive track 110b.

The multiple-layer element of the present invention can be used to determine the concentration of numerous analytes. However, the element is particularly useful for determining the concentration of ALT in whole blood.

Accordingly, discussion of the reagents will focus primarily on reagents that are useful for determining the concentration of ALT in whole blood.

The reagent layer 114 overlies the detecting layer 102 and contains those reagents necessary for the reaction with analyte in the biological fluid to produce a reaction product, which is detected at the working electrode 104. In the case of ALT, the reaction product is typically hydrogen peroxide, but it could be glutamate. The reagent layer 114 is soluble upon contact with the biological fluid. The reagent layer 114 comprises a mixture of reagents, comprising (1) at least one substrate with which the ALT reacts and, optionally, (2) at least one enzyme with which the reaction product(s) of ALT and the substrate(s) react. Substrates with which the ALT reacts include, but are not limited to, the following: L-alanine, alpha-ketoglutarate. Enzymes with which the reaction product of ALT and the substrate(s) can react include, but are not limited to, glutamate oxidase and pyruvate oxidase. Cofactors that help to activate the ALT enzyme include, but are not limited to, pyridoxal-5'-phosphate. The reagent layer 114 may also contain an anticoagulant. Anticoagulants include, but are not limited to, heparin, oxalate, citrate, and EDTA. The anticoagulant should be present in an amount sufficient to prevent the sample of blood from coagulating during the period of measurement. A typical formulation for preparing the reagent layer 114 comprises the following ingredients in the amounts indicated, based on final concentrations when dissolved in blood:

| L-alanine | 0.5 M/L |
| alpha-ketoglutarate | 10 mM/L |
| pyridoxal 5'-phosphate | 13 $\mu$M/L |
| glutamate oxidase | 2 U/mL |
| trehalose | 10 mM/L |

In the preferred embodiments, a fluid-transporting layer 116, which typically comprises a surfactant-coated layer of mesh, may be placed over the detecting layer 102. The fluid-transporting layer 116 provides for chemically aided wicking of the sample to the electrodes. The fluid-transporting layer 116 extends to a sample application zone 118 of a covering layer 120. The sample application zone 118 is characterized by an opening that allows access of the sample to the underlying fluid-transporting layer 116. The covering layer 120 is liquid impermeable. The fluid-transporting layer 116 is maintained in a fixed position by an overcoat layer 122, which both defines the area of the electrodes exposed to biological fluid, e.g., blood, and serves as an electrical insulating layer. The covering layer 120 also serves to enclose the electrodes to prevent evaporation of the sample during the measurement, which requires several minutes.

The fluid-transporting layer 116 is preferably made from polymeric material, cellulosic material, natural fibrous material, or an equivalent material. Representative examples of polymeric materials suitable for the fluid-transporting layer of this invention include, but are not limited to, polymers comprising amide monomeric units, e.g., nylon, ester monomeric units, alkylene monomeric units, e.g., polypropylene, polyethylene, cellulosic monomeric units, and combinations thereof. The fluid-transporting layer can be a mesh. The mesh is preferably constructed of finely woven strands of polymeric material; however, any woven or non-woven material may be used, provided that the fluid-transporting layer transports the blood to the detecting layer 102 before the blood evaporates or clots. A fine mesh that is suitable for the multiple-layer element of this invention has a percent open area of from about 40 to about 45%, a mesh count of from about 95 to about 115 fibers per cm, a fiber diameter of from about 20 to about 40 μm, and a thickness of from about 40 to about 60 μm. A particularly preferred mesh is NY64 HC mesh, available from Sefar (formerly ZBF), CH-8803, Ruschlikon, Switzerland. A coarse mesh that is suitable for the multiple-layer element of this invention has a percent open area of from about 50 to about 55%, a mesh count of from about 45 to about 55 fibers per cm, a fiber diameter of from about 55 to about 65 μm, and a thickness of from about 100 to about 1000 μm. A preferred mesh is NY151 HC mesh, available from Sefar (formerly ZBF), CH-8803, Ruschlikon, Switzerland. Mesh characteristics are further described in U.S. Pat. No. 5,628,890, incorporated herein by reference.

The fluid-transporting layer 116 transports blood by means of a chemically aided wicking action. As used herein, the expression "chemically aided wicking action" refers to either:

(a) the flow of fluid along a material wherein the nature of the material itself is hydrophilic, such as, for example, cellulose; or (b) the flow of fluid along a material wherein at least one chemical substance is applied to the surface of the material, such as, for example, nylon coated with surfactant; or (c) the flow of fluid along a material that has been rendered hydrophilic by means of a chemical or physical process, such as, for example, treatment of polyester by means of corona discharge treatment, plasma treatment, flame treatment, or the like.

The purpose of the at least one chemical substance applied to the surface of the material of the fluid-transporting layer 116 is to promote the flow of fluid along the surface of the material. Chemical substances suitable for the foregoing purpose belong to the class of compounds commonly referred to as surfactants. Surfactants reduce the surface tension of the surface upon which they are coated and allow the coated surface to attract rather than repel fluids. A commercially available surfactant suitable for use in this invention is a fluorochemical surfactant having the trade designation "FC 170C FLUORAD", available from Minnesota Mining and Manufacturing Company, St. Paul, Minn. This surfactant is a solution of a fluoroaliphatic oxyethylene adduct, lower polyethylene glycols, 1,4-dioxane, and water. It has been found that approximately 1 to 10 μg surfactant per mg of fluid-transporting layer is preferred. The preferred surfactant loading may vary depending upon the nature of the material of the fluid-transporting layer and the surfactant used. The preferred amount can be determined empirically by observing flow of sample along the fluid-transporting layer with different levels of surfactant loading. The surfactant may not be necessary if the mesh is made of hydrophilic material. The thickness and the properties of the material of the fluid-transporting layer 116 will determine its strength.

The fluid-transporting layer 116 is capable of allowing a sufficient amount of fluid, e.g., blood, to uniformly flow through it at a rate sufficiently great that a sufficient amount of fluid, e.g., 0.1 to 10 μl, preferably up to 5 μl, more preferably up to 3.5 μl, reaches the detecting layer 102 before evaporation or coagulation causes the size of the sample to be inadequate to provide a reading of analyte level within a reasonable time, e.g., up to five minutes. The fluid-transporting layer 116 can be adhered to the covering layer 120 by means of hot melt adhesive on the major surface of the covering layer 120 that faces the meter-contactable layer 108.

The covering layer 120 is preferably formed from a hydrophobic material. The covering layer 120 is preferably sufficiently flexible to conform to the remaining layers of the multiple-layer element 100.

Representative examples of materials that are suitable for preparing the covering layer 120 include, but are not limited to, polymeric materials, such as polyesters, polyimides, polyethylenes, polypropylenes, polycarbonates, polyacrylics, and combinations thereof.

The thickness of the covering layer 120 is not critical, but preferably ranges from about 0.005 mm to about 2.0 mm. The surface dimensions of this layer are not critical, but the major surface dimension preferably ranges from about 5 mm to about 60 mm and the minor surface dimension preferably ranges from about 2 mm to about 30 mm. The layer is shown as being elongated and rectangular, but other shapes are also suitable, e.g., circular, elliptical, triangular, square, and other shapes. Although the embodiment in FIG. 1A displays a covering layer, it is possible, but not preferred, to dispense with the covering layer entirely.

The covering layer 120 and the fluid-transporting layer 116 are preferably arranged in such a way that blood is not impeded from reaching the fluid-transporting layer by the covering layer. The fluid-transporting layer 116 is disposed between the covering layer 120 and the meter-contactable layer 108.

The detecting layer 102 provides for detection of the $H_2O_2$ or glutamate produced by the reaction of ALT with components in the reagent layer. The working electrodes preferably comprise a member selected from the group consisting of carbon, platinum, gold, palladium, silver chloride, and silver. The working electrode may have enzymes, e.g., peroxidase or glutamate oxidase, immobilized on or deposited over the surface thereof. As stated previously, a typical detecting layer comprises a first conductor and a second conductor extending along a support and further comprises a means for connection to circuitry for readout of the measurement. The working electrode is positioned to contact the liquid blood sample and the first conductor. The ALT in the blood sample reacts with the reagents in the reagent layer 114 to produce a product that is detected at the working electrode 104. Electrons are transferred between the enzyme-catalyzed reaction and the first conductor to create the current. A reference electrode 106 is positioned to contact the liquid blood sample and the second conductor. The reference electrode 106 completes the electrical circuit.

In one preferred embodiment of a detecting layer 102 for the multiple-layer element of this invention, a redox polymer is coated over the working electrode 104. In another preferred embodiment, the working electrode 104 comprises a peroxidase enzyme/carbon mixture that is not capable of being dissolved by blood. In another preferred embodiment of the detecting layer, an electron mediator, e.g., a ferrocene, is included in the working electrode deposit to effect the electron transfer. The working electrode 104 and the reference electrode 106 are coatings applied to the meter-contactable layer 108. For example, the working electrode 104 is formed by printing (e.g., screen printing) an ink comprising a conductive compound. The enzyme needed to react with the product of the ALT reaction, e.g., glutamate oxidase, is applied to the working electrode 104 or it may be part of the reagent layer that is deposited over the working electrode 104. This reagent layer may contain alanine, alpha-ketoglutarate, pyridoxal 5'-phosphate, and an anticoagulant. The reference electrode 106 is also formed by printing (e.g., screen printing). The means for connecting to the readout circuit are positioned toward one end of the meter-contactable layer 108, and the electrodes are positioned remote from that end. Additional variations of the foregoing embodiment are described in the previously incorporated U.S. Pat. No. 5,682,884.

The meter-contactable layer 108 is preferably made from a polymeric material. Representative examples of polymeric material suitable for preparing the meter-contactable layer include polymers comprising acrylic monomeric units, methacrylic monomeric units, acrylate monomeric units, methacrylate monomeric units, vinyl chloride monomeric units, and combinations of the foregoing. Other polymers suitable for preparing the meter-contactable layer include polyesters. The functions of the meter-contactable layer are to (1) provide a surface on which to print the detecting layer 102, (2) provide contact of the multiple-layer element 100 with the meter for the purpose of reading the signal from the detecting layer 102 of the multiple-layer element 100, (3) provide a rigid layer so that the multiple-layer element 100 can be easily picked up and placed in contact with the meter.

The following table lists suitable ranges for the dimensions of the layers of the multiple-layer element of this invention. It is not intended that the dimensions of the layers of the multiple-layer element of this invention be limited to the ranges listed in the following table.

| Layer | Major surface dimension (mm) | Minor surface dimension (mm) | Thickness (mm) |
| --- | --- | --- | --- |
| Covering | 5 to 60 | 2 to 30 | 0.005 to 2.0 |
| Fluid-transporting | 5 to 60 | 2 to 30 | 0.005 to 0.5 |
| Reagent | 5 to 60 | 2 to 30 | 0.001 to 0.5 |
| Detecting | 5 to 60 | 2 to 30 | 0.001 to 0.5 |
| Meter-contactable | 5 to 60 | 2 to 30 | 0.05 to 2.0 |

The surface dimensions, e.g., length, of the fluid-transporting layer 116 are preferably less than those of the layer on which the detecting layer 102 is printed, so that, the electrical contacts 113a, 113b on the detecting layer 102 are exposed to facilitate insertion into the meter.

The surface dimensions, e.g., length, of the meter-contactable layer 108 are preferably larger than those of the covering layer 120 so that electrical contacts are exposed to facilitate insertion into the meter.

The multiple-layer element 100 is preferably sufficiently rigid so that it can be easily handled by the user. In the preferred embodiments, the meter-contactable layer 108 is made of a material that is sufficiently rigid to support the fluid-transporting layer 116 and the covering layer 120. The last two mentioned layers can be extremely flexible and of minimal rigidity.

The porosities of the layers of the multiple-layer element 100 are dependent upon the positioning and functionality of the layer. The covering layer 120 and the meter-contactable layer 108 are preferably sufficiently non-porous to form a well or chamber for the blood. The fluid-transporting layer 116 is preferably sufficiently porous to allow blood to flow uniformly and rapidly therethrough to the detecting layer 102.

As stated previously, an optional overcoat layer 122 (see FIG. 1A) can be interposed between the covering layer 120 and the meter-contactable layer 108 to restrict the flow of blood in the fluid-transporting layer 116. The overcoat layer 122 can be prepared by means of a material that is initially in a liquid form or in a form capable of penetrating the interstices of a mesh. This material is preferably a hydrophobic electrically insulating ink. This material is preferably applied by screen printing over a portion of the periphery of the fluid-transporting layer 116 (which is preferably in the form of a mesh), thereby surrounding and defining a suitable path for the sample of blood to travel from the point it contacts the fluid-transporting layer 116 to the detecting layer 102. See U.S. Pat. No. 5,628,890 for additional discussion concerning how the overcoat layer holds down and fixes the mesh layer in place. The overcoat layer 122 and the fluid-transporting layer 116 are substantially coplanar. As used herein, the term "coplanar" means that at least one surface of each of two materials resides in the same plane. Substantial coplanar positioning of these layers is preferred because the fluid-transporting layer 116 spreads blood in all directions. In order to limit the spread of blood in undesired areas of the multiple-layer element, the overcoat layer 122 acts as a barrier to flowing blood. The fluid-transporting layer 116 is adhered to the meter-contactable layer 108 by means of embedding the edges of the fluid-transporting layer 116 with the overcoat layer 122. As used herein, the expression "substantially coplanar" includes both the situation wherein at least one major surface of the overcoat layer 122 and at least one major surface of the fluid-transporting layer 116 are in the same plane and the situation wherein at least one major surface of the overcoat layer 122 extends slightly beyond at least one major surface of the fluid-transporting layer 116. True coplanarity, i.e., the former situation, is difficult to achieve primarily because of manufacturing conditions. Substantial coplanarity, i.e., the latter situation, is more likely to be achieved under actual manufacturing conditions. However, it is preferred that the overcoat layer 122 and the fluid-transporting layer 116 approach true coplanarity as much as possible so that the volume of blood needed to be extracted is as small as possible. See PCT International Application WO 98/24366, incorporated herein by reference.

FIG. 1B illustrates another embodiment of the biosensor of this invention. FIG. 1B shows a biosensor 100 that comprises a meter-contactable layer 108 having a sample application zone 118, a covering layer 120, a reagent layer 114, a fluid-transporting layer 116, and an overcoat layer 122. FIG. 1B does not show the detecting layer. The detecting layer, which is present but hidden in FIG. 1B, is disposed on the major surface of the meter-contactable layer 108 that faces the overcoat layer 122. Like the biosensor shown in FIG. 1A, the detecting layer of the biosensor 100 in FIG. 1B comprises a working electrode, a reference electrode, conductive tracks, and electrical contacts. In FIG. 1B, the reagent layer 114 is disposed between the fluid-transporting layer 116 and the major surface of the meter-contactble layer 108 that faces the overcoat layer 122. Each component of the biosensor 100 in FIG. 1B, both those components that are shown and those components that are hidden, have the same functions and materials of construction as do the corresponding components in FIG. 1A. For this reason, the reference numerals of the components in FIG. 1B are identical to the reference numerals of the corresponding components in FIG. 1A.

The ALT sensors of this invention can employ several types of chemical reactions. Five representative examples of chemical reactions for the ALT biosensor are described below.

Example Reaction 1

Oxidation of $H_2O_2$ at Electrode Surface

The working electrode comprises a metal. A reagent layer overlying the working electrode contains the following reagents: L-alanine, α-ketoglutarate, and glutamate oxidase.

Reaction (1)

Reaction (2)

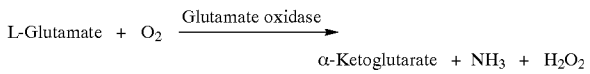

Reaction (3)

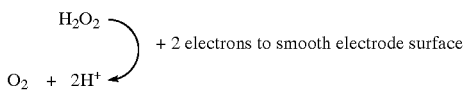

In reaction (1), ALT in the blood catalyzes a reaction in which an amino group from the substrate, L-alanine, is transferred to α-ketoglutarate to produce the products: pyruvate and L-glutamate. Reaction (1) is reversible. In reaction (2), glutamate oxidase oxidizes L-glutamate, produced in reaction (1), to form α-ketoglutarate, $NH_3$, and $H_2O_2$ (hydrogen peroxide). In reaction (3), $H_2O_2$ produced in reaction (2), is oxidized to $O_2$ and $2H^+$ at the electrode surface. The oxidation of $H_2O_2$ is catalyzed by the electrode's metal surface poised at an oxidizing potential. Two electrons are released from this reaction resulting in current. The amount of current generated at the electrode is proportional to the amount of $H_2O_2$ produced in reaction (2), which, in turn, is proportional to the amount of glutamate produced in reaction (1), which, in turn, is proportional to the amount ALT in the blood sample.

Example Reaction 2

Electrode with Peroxidase Redox Polymer

The working electrode comprises a metal or carbon electrode and a redox polymer coating. The redox polymer coating is a cross-linked structure that has peroxidase (HRP) immobilized in it. The redox polymer also contains metal centers, such as osmium (Os), which can accept and donate electrons to the polymer coating. Electrons can be efficiently transferred within this redox polymer coating between the Os metal centers and the peroxidase enzyme. The redox polymer coating electrically connects peroxidase to the metal or carbon electrode surface, i.e., electrons can be efficiently transferred between peroxidase and the electrode surface. A reagent layer overlying the working electrode contains the following reagents: L-alanine, α-ketoglutarate, and glutamate oxidase.

Reaction (1)

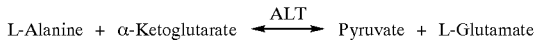

Reaction (2)

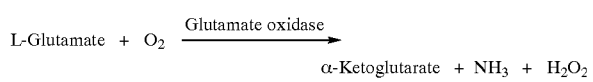

Reaction (3)

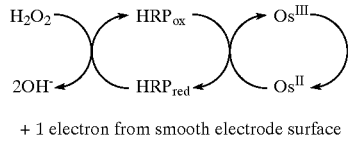

+ 1 electron from smooth electrode surface

In reaction (1), ALT in the blood catalyzes a reaction in which an amino group from the substrate, L-alanine, is transferred to α-ketoglutarate to produce the products: pyruvate and L-glutamate. Reaction (1) is reversible. In reaction (2), glutamate oxidase oxidizes L-glutamate, produced in reaction (1), to form α-ketoglutarate, $NH_3$, and $H_2O_2$ (hydrogen peroxide). In reaction (3), $H_2O_2$ oxidizes peroxidase in the redox polymer. Peroxidase is then reduced by electrons donated from the Os center. This reaction results in the oxidation of the Os center in the polymer from Os" to Os"'. The oxidized Os center is then re-reduced by electrons originating at the electrode at the correct potential (0 to 200 mV). The re-reduction of the Os center, and, consequently, the peroxidase, results in the generation of current. The amount of current generated at the electrode is proportional to the amount of $H_2O_2$ produced in reaction (2), which is, in turn, proportional to the amount of glutamate produced in reaction (1), which is, in turn, proportional to the amount ALT in the blood sample.

Example Reaction 3

Electrode with Glutamate Oxidase Redox Polymer

The working electrode comprises a metal or carbon and a redox polymer coating. The redox polymer coating is a cross-linked structure that has glutamate oxidase (GLOX) immobilized therein. The redox polymer also contains metal centers, such as osmium (Os), which can accept and donate electrons to the polymer coating. Electrons can be efficiently transferred within this redox polymer coating between the Os metal centers and the GLOX enzyme. The redox polymer coating electrically connects GLOX to the metal or carbon of the surface of the electrode, i.e., electrons can be efficiently transferred between GLOX and the surface of the electrode. A reagent layer overlying the working electrode contains the following reagents: L-alanine and α-ketoglutarate.

Reaction (1)

Reaction (2)

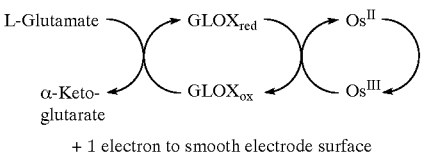

+ 1 electron to smooth electrode surface

In reaction (1), ALT in the blood catalyzes a reaction in which an amino group from the substrate, L-alanine, is transferred to α-ketoglutarate to produce the products: pyruvate and L-glutamate. Reaction (1) is reversible. In reaction (2) glutamate reduces GLOX in the redox polymer. GLOX is then oxidized by the Os metal center. This reaction results in the reduction of the Os center in the polymer from Os'" to Os". The reduced Os center is then re-oxidized when it releases an electron at the electrode surface at the correct potential (100 to 300 mV). The re-oxidation of the Os center, and, consequently, the GLOX enzyme, results in the generation of current. The amount of current generated at the electrode is proportional to the amount of glutamate produced in reaction (1), which is, in turn, proportional to the amount of ALT in the blood sample.

Example Reaction 4

Electrode with a Mediator

The working electrode comprises metal or carbon. A reagent layer overlying the working electrode contains the following reagents: L-alanine, α-ketoglutarate, GLOX, and a mediator. The mediator can transfer electrons from the non-electrochemically active species (GLOX) to the electrochemically active component (the electrode).

Reaction (1)

Reaction (2)

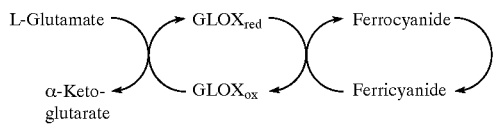

Reaction (3)

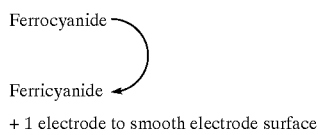

+ 1 electrode to smooth electrode surface

In reaction (1), ALT in the blood catalyzes a reaction in which an amino group from the substrate, L-alanine, is transferred to α-ketoglutarate to produce the products, pyruvate and L-glutamate. Reaction (1) is reversible. In reaction (2), glutamate reduces GLOX. GLOX is then oxidized by reacting with the mediator; ferricyanide. This reaction results in the reduction of ferricyanide to ferrocyanide. The ferrocyanide is then re-oxidized to ferricyanide when it reacts with the working electrode at the correct potential (300 to 500 mV). An electron is released in this reaction resulting in current. The amount of current generated at the electrode is proportional to the amount of glutamate produced in reaction (1), which is, in turn, proportional to the amount of ALT in the blood sample. It should be noted that the mediator not limited to ferricyanide.

Example Reaction 5

Peroxidase in the Smooth Electrode

The working electrode comprises a carbon electrode having an enzyme, peroxidase, incorporated within it. Electrons can be efficiently transferred between the carbon particles that make up the electrode and peroxidase incorporated within the electrode. A reagent layer overlying the working electrode contains the following reagents: L-alanine, α-ketoglutarate, and GLOX.

Reaction (1)

Reaction (2)

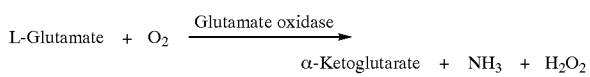

Reaction (3)

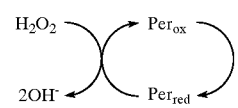

+ 1 electron originating within the electrode

In reaction (1), ALT in the blood catalyzes a reaction in which an amino group from the substrate, L-alanine, is transferred to α-ketoglutarate to produce the products, pyruvate and L-glutamate. Reaction (1) is reversible. In reaction (2), glutamate oxidase oxidizes L-glutamate, produced in reaction (1), to form α-ketoglutarate, $NH_3$, and $H_2O_2$ (hydrogen peroxide). In reaction (3), $H_2O_2$ oxidizes peroxidase (Per) contained within the working electrode. Peroxidase is then re-reduced by electrons originating in the electrode at the correct potential (0 to 100 mV). This results in the generation of current, which is proportional to the amount of $H_2O_2$ produced in reaction (2), which is, in turn, proportional to the amount of glutamate produced in reaction (1), which is, in turn, proportional to the amount ALT in the blood sample.

Method for Preparing the Multiple-Layer Element

The multiple-layer element is preferably mass-produced. However, the following method can be used for the manufacture of a single multiple-layer element.

The meter-contactable layer 108 can be provided in the form of a sheet. In a typical construction, the meter-contactable layer 108 can be a sheet of polyvinyl chloride. The conductive tracks 110a, 110b may be sputtered onto the meter-contactable layer or applied in another manner, such as screen-printing. The electrodes 104, 106 can be screen printed onto the meter-contactable layer 108. An electrode containing the redox polymer can be prepared in the following manner. First, a solution containing a surfactant is dispensed over the working electrode and allowed to dry. The redox polymer, which is provided in the form of a liquid, is dispensed over the layer of dried surfactant on the working electrode at a volume of 0.07 $\mu L/mm^2$ and is allowed to cure overnight at ambient conditions. The reagent layer 114 can then be deposited onto the detecting layer 102 by means of an appropriate coating technique, e.g., drop coating.

The fluid-transporting layer 116 is then placed in a position such that it will be in fluid communication with the detecting layer 102. The covering layer 120 can then be adhered to the fluid-transporting layer 116 and the meter-contactable layer 108 by means of a hot-melt adhesive.

The anticoagulant may be coated onto the fluid-transporting layer 116 that extends over the electrodes, may be dispensed over the electrodes, may be contained in the blood application area, or any combination of the foregoing.

Operation

FIGS. 1A and 1B illustrate the components of the multiple-layer element in detail. The blood is collected on the sample application zone 118 of the biosensor and may be transported via the fluid-transporting layer to the electrodes 104, 106 by means of a chemically aided wicking action.

The sample, e.g., blood, contacts the fluid-transporting layer 116, flows along the fluid-transporting layer 116 until it reaches the reagent layer 114. The reagent layer 114 dissolves upon exposure to the blood sample, thereby exposing the detecting layer 102 to the sample. A chemical reaction occurs at the detecting layer 102. The output of the chemical reaction can be read at the electrical contacts 113a, 113b of the detecting layer 102.

The meter-contactable layer 108 must physically contact the meter (not shown) in order to have the sensor, i.e., the detecting layer 102, make electrical contact with the meter, such as by insertion into an electrical connector.

While not preferred, it is also possible to provide a workable multiple-layer element that dispenses with the fluid-transporting layer 116. In order to eliminate the fluid-transporting layer 116, the meter-contactable layer 108 and the covering layer 120 can be disposed in such a manner that blood can flow between them to the detecting layer 102 by means of capillary action. In one embodiment involving flow by means of capillary action, the major surface of the meter-contactable layer 108 facing the major surface of the covering layer 120 and the major surface of the covering layer 120 facing the major surface of the meter-contactable layer should be hydrophilic in nature. At least one of the foregoing major surfaces, and preferably both of the foregoing major surfaces, can either be made of a hydrophilic material or can be coated with a hydrophilic material, such as, for example, a surfactant. The hydrophilicity of these layers will cause the fluid applied to the sample application zone 118 to flow in the space between the meter-contactable layer 108 and the covering layer 120 to the detecting layer 102. Thus, it is clear that the fluid-transporting layer 116 can be eliminated. In this embodiment, the meter-contactable layer 108 must be of sufficient length so that a capillary channel can be formed between the meter-contactable layer 108 and the covering layer 120. The capillary channel can be, in effect, formed by means of the overcoat layer 122, which causes a space of capillary width to be formed between the meter-contactable layer 108 and the covering layer 120.

By using the multiple-layer element 100 of this invention, the ALT assay can be carried out in a highly efficient manner to evaluate a patient's liver function. Applications for which this rapid and simple assay can be used include the following.

(1) monitoring patients who are on medication that requires regular evaluations of liver function;
(2) monitoring liver function during clinical trials for new drugs;
(3) screening potential blood donors for elevated liver enzymes, which may indicate hepatitis infection;
(4) diagnosing and treating of patients with hepatitis, other liver diseases, and heart diseases; and
(5) evaluating or monitoring workers who may be exposed to agents that damage the liver.

The biosensor of this invention includes an anticoagulant to prevent the blood from clotting during the chemical reaction. Because the concentration of ALT in blood is so low, a reaction time of several minutes is required in order for a measurable signal to be generated. However, blood begins to coagulate in approximately one minute. The reagents used in U.S. Pat. No. 5,705,045 (Park) are confined in layers that are screen-printed over the sensor, with the result that the reagents cannot be used to prevent the blood sample from coagulating. The biosensor of the present invention is specifically designed so that whole blood from a fingerstick can be applied directly to the biosensor, thereby eliminating the need for a person trained in drawing blood and making the assay sufficiently simple so that patients can run it by themselves.

In order to improve the peroxide signal of the biosensor of U.S. Pat. No. 5,705,045 (Park), a screen printed, porous, layer carbon, which had a larger surface area than did a smooth layer of carbon, was used. The porous surface allowed the peroxide to contact a larger surface area than would a smooth surface and the result was a signal of greater magnitude. Unfortunately, the greater surface area also resulted in a greater background signal. A porous carbon layer can increase a signal by a factor of 100, but the time required for the background signal of the electrode to stabilize increases from seconds to minutes. A smooth electrically conductive electrode made from a pure metal will stabilize much more rapidly, thereby decreasing the duration of the assay.

One of the major sources of error in the measurement of analytes present at low concentration, such as ALT, is the variability of the surface roughness of the electrically conductive surface that forms all or part of the detecting layer. When a voltage is applied to any electrically conductive surface that is in contact with a fluid, a current is generated. That current is referred to as the double layer charging current. The surface of the metal and the solution with which it is in contact achieve opposite polarities in response to the applied potential. The excess charge on the is metal resides at its surface. The solution dissipated its charge over many ordered layers of ions that orient themselves opposite to the charge on the metal. The metal achieves its potential almost instantaneously, because it has a large supply of mobile electrons in the conduction band of the metal. The solution capacitance is formed more slowly, because it relies on the diffusion of ions in solution. The surface of the electrode functions in a manner similar to that of an electrolytic capacitor. The current required to charge this capacitor is given by the following equation:

$$i = (E/R)e^{(-t/RC_d)} \qquad (1)$$

where
i=double layer charging current
E=applied potential
R=resistance of the biosensor and solution
t=time
$C_d$=double layer capacitance The applied potential, E, is fixed for each determination and typically remains constant between determinations. The resistance is also typically constant between determinations. The double layer capacitance is, however, directly proportional to the roughness of the surface of the electrode. The entire surface of the metal in contact with the solution is at the same potential. The rougher the surface the more solution is in direct contact with the surface and must become charged. The charging current will then be directly affected by the roughness of the electrode.

The measurement of concentrations of analytes in blood present in low concentration, such as ALT, will require reproducible and low background signals. As the roughness of the electrode increases the double layer charging current will increase. If the surface of the electrode is too rough, measurement of the ALT current will become difficult for the following reasons:

(1) Accurately measuring a small ALT current, which is now combined with a large double layer charging current, will be difficult.

(2) Small changes in the ALT current will be difficult to detect if they are superimposed on a much larger charging current.

(3) A small change in a large signal is often difficult to detect because less sensitive electronics has to be used to detect larger currents.

(4) The less sensitive electronics cannot detect small current changes as accurately as can more sensitive electronics, which could be used if the double layer charging current was small relative to the ALT current.

Non-reproducibility in the smoothness of the surface of the electrode will also cause non-reproducibility of the ALT signal. Because the measured signal is a combination of the ALT current and the double layer charging current, any irreproducibility in the double layer charging current will cause the measured current to be irreproducible. The larger the double layer charging current relative to the ALT current, the worse the problem becomes. It is therefore necessary to have a smooth electrode in order to lessen the effect that double layer charging will have on the ALT signal and to obtain reliable ALT measurements.

The smoothness required for the metal surface to accurately detect the small currents resulting from analytes present at low concentrations is determined by several factors.

As can be readily seen by examining equation 1, the double layer charging current decays exponentially with time. The current attributable to the analyte typically decays with time at a much slower rate or may actually increase with time. Applying a potential and waiting a relatively long time will allow the double layer charging current to decay. The time at which the analyte measurement must be made is therefore an important factor in deciding how smooth the electrode needs to be. Although the problems of roughness and double layer charging could be overcome by waiting long times, this solution is not practical for whole blood measurements. Given a sufficiently long time, whole blood will separate into plasma and red blood cells. Cell membranes will begin to leak, thereby causing analyte concentrations to change. Cell metabolism can change analyte concentrations. In the analysis of samples of whole blood, the time available for analysis is necessarily short.

The concentration of the analyte is another factor that will determine the smoothness required for an accurate measurement. The lower the concentration of the analyte, and, consequently the current generated by the analyte, the smoother the electrode will need to be.

Another factor that will determine the smoothness required is the level of accuracy needed for the measurement of the concentration of the analyte. Each analyte requires that the measurement be made to a certain level of accuracy in order that the measured result is meaningful. This is best understood by examples of analytes in the field of medical diagnostics. When an analyte reaches a certain medically determined decision point, a doctor will take a certain course of action with a patient. The determination of the analyte concentration around those decision points needs to be relatively accurate for the doctor to make treatment decisions with confidence. Because those decision points vary with each analyte, the requirement for accuracy needs to be specified for each analyte. Consequently the level of smoothness would also have to be specified for each analyte to meet the accuracy need for each decision point. The easiest factor to quantify regarding the double layer charging current and the current attributable to the analyte is the magnitude of one versus the other. If the magnitude of the double layer charging current approaches the magnitude of the current attributable to the analyte, then an accurate measurement is likely to be difficult. At equal levels of current, a 10% variation in the double layer signal would cause a 5% change in the total current. A 5% change in signal and the consequent error in the analyte determination would be of concern for most medical analytes. Example 6 demonstrates the effect of smoothness of the surface of the working electrode on the ALT assay.

The difficulty caused by the double layer charging current in making an accurate measurement is much more severe when a dissolving binder is used to form the working electrode. Such a dissolving binder system for the working electrode is the basis of U.S. Pat. No. 5,705,045. The dissolving binder continuously exposes previously dry metal to the solution throughout the course of the analyte determination. A current is drawn by each conductive particle as it is exposed to solution.

The scheme of dissolving binders as proposed by in U.S. Pat. No. 5,705,045 is therefore a poor design for an ALT sensor. The design of this invention is clearly superior to that disclosed in U.S. Pat. No. 5,705,045 because the need for a dissolving metal binder has been eliminated. One of the two chemical reactions proposed in U.S. Pat. No. 5,705,045 (Park) suggests using NAD in the ALT reaction. This chemical system is inferior to one that produces peroxide, because NAD is both expensive and unstable. The chemical reaction of this invention, which produces peroxide, does not require NAD and is therefore preferred. This invention employs chemically aided wicking to transport the sample from the sample application zone to the electrodes. U.S. Pat. No. 5,705,045 (Park) relies on capillary action to move the sample from the sample application zone to the electrodes. The sample must be allowed to react with the reagent at the electrode for several minutes in order for a measurable signal to be generated. The sample must not be allowed to evaporate during this time in order for an accurate reading to be obtained. Transporting the sample from the sample application zone to the electrodes in a manner so that the sample will be prevented from evaporating is a critical step in the process of this invention.

In this invention, the reagents for the reagent layer need not be screen-printed in the form of a paste over the electrodes. The reagents of the reagent layer can be dropped onto the electrode as a liquid and allowed to dry. Screen-printing is more complicated than dropping a liquid onto the electrodes. Screen-printing requires tight tolerances in order for the results to be precise. This invention uses standard liquid dispensing techniques, which do not require tight tolerances, and consequently provides a simpler manufacturing process.

This invention does not require the precise addition of a liquid reagent and does not suffer from accuracy problems associated with errors in the addition of a liquid reagent. This invention will work well with a sample of whole blood.

This invention requires a working electrode that has a smooth electrically conducting surface, preferably made of a pure metal, to measure the peroxide produced by the reaction of the reagents in the reagent layer with the liver enzyme. Because the concentration of the liver enzyme in the blood is very small, the amount of peroxide produced is very small. In order to detect low concentrations of peroxide, a metal surface that is very efficient at oxidation of peroxide is required. A pure metal having a smooth surface, such as platinum or palladium, can provide such a surface. Platinum is 19 times better at the oxidation of peroxide than carbon. An ALT biosensor having a working electrode made of platinum or another pure metal would be far superior to an ALT biosensor having a working electrode made of carbon. Other examples of materials suitable for forming a smooth, electrically conductive surface include gold, silver, and silver chloride. A working electrode made of carbon and having a smooth surface can be used with the addition of a redox polymer or the inclusion of an enzyme in the electrode. The addition of the redox polymer or the inclusion of the enzyme improves the performance of the carbon electrode so that its performance is similar to that of an electrode made of pure metal.

The following non-limiting example further illustrate features of the present invention.

EXAMPLES

Example 1

Figure 3:
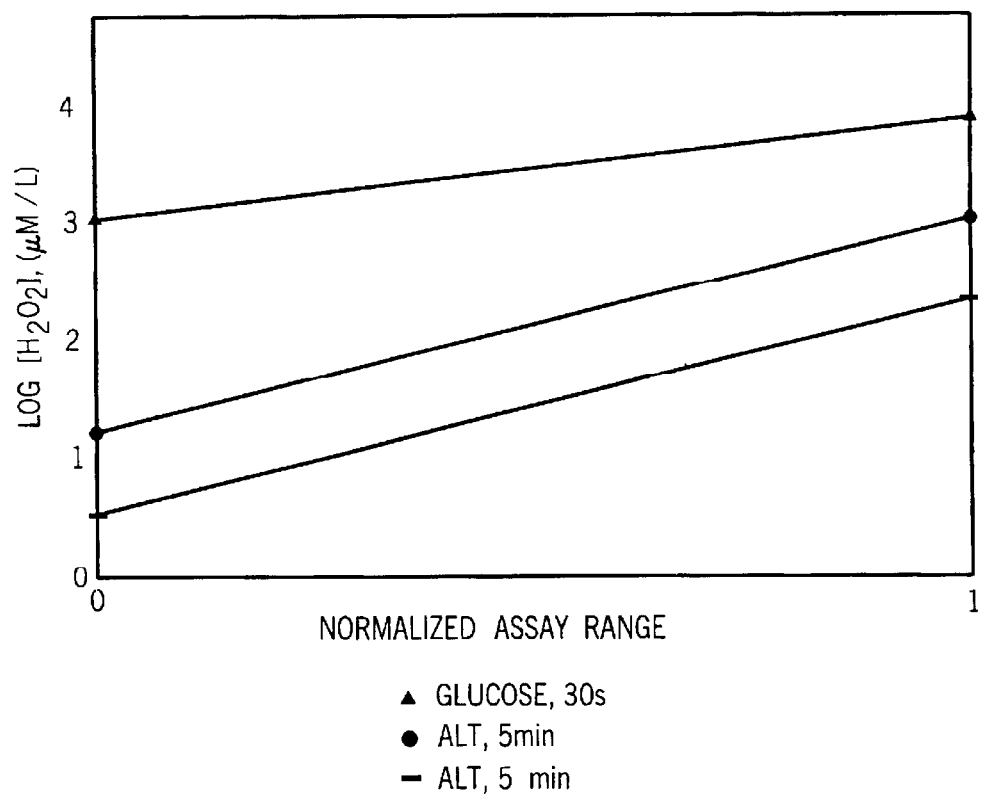
FIG. 3 is a graph comparing the quantity of peroxide produced from the enzymatic reaction of glucose with the quantity of peroxide produced from the enzymatic reaction of ALT.

FIG. 3 illustrates the quantity of peroxide produced from the enzymatic reaction of glucose with quantity of peroxide produced from the ALT enzymatic reaction via the following reaction pathways:

ALT Reaction:

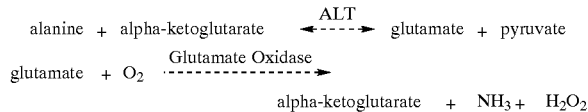

Glucose Reaction:

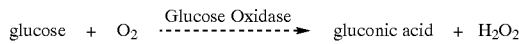

The glucose reaction pathway shown above is typically used in commercially available electrochemically-based blood glucose assays. An ALT enzymatic reaction allowed to proceed for five minutes will generate peroxide concentrations up to nearly two orders of magnitude lower than peroxide concentrations generated from enzymatic reaction of glucose allowed to proceed 30 seconds. The foregoing data demonstrate that ALT is present at much lower concentrations in blood than is glucose.

Example 2

Figure 2:
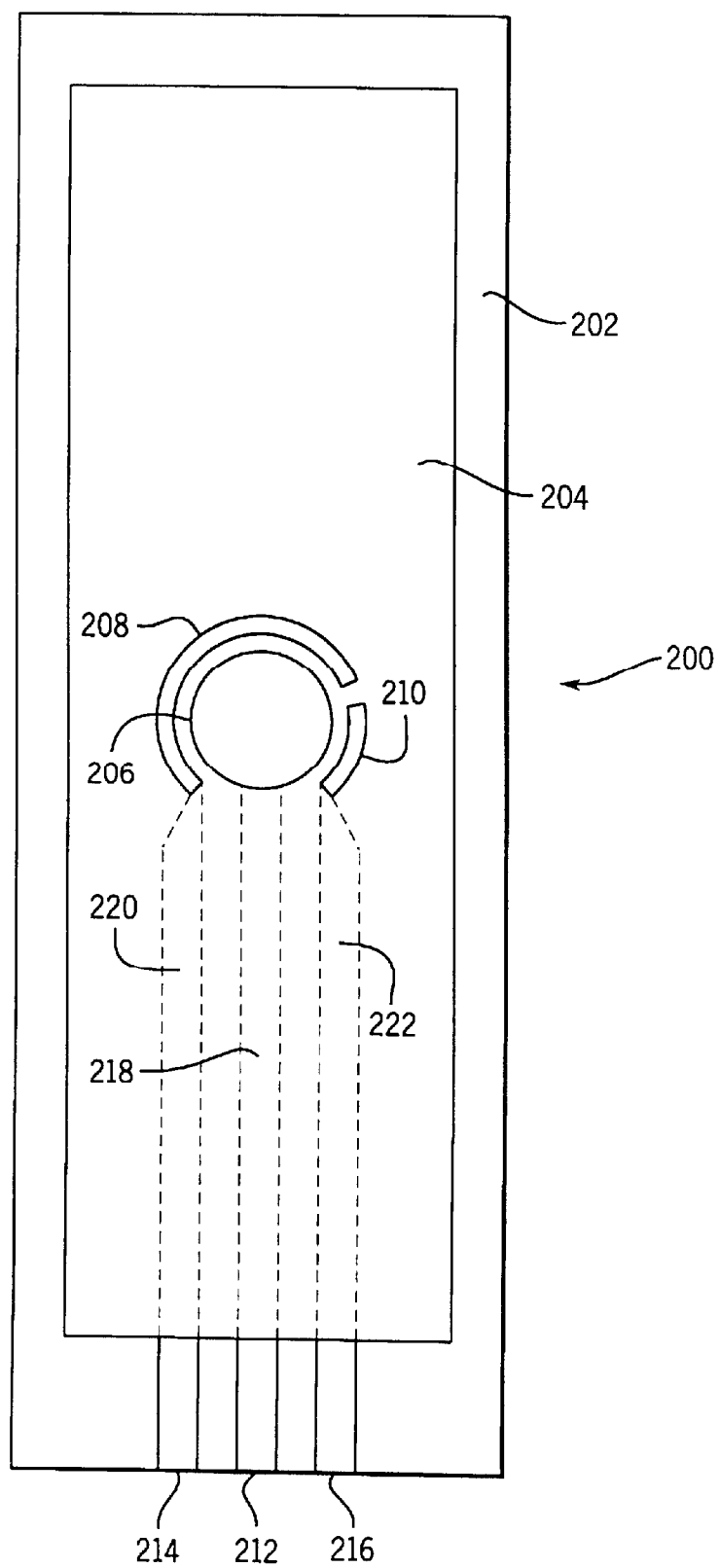
FIG. 2 is a top plan view of a biosensor of the type used to generate data in Examples 2, 4, 5, and 6.
Figure 4:
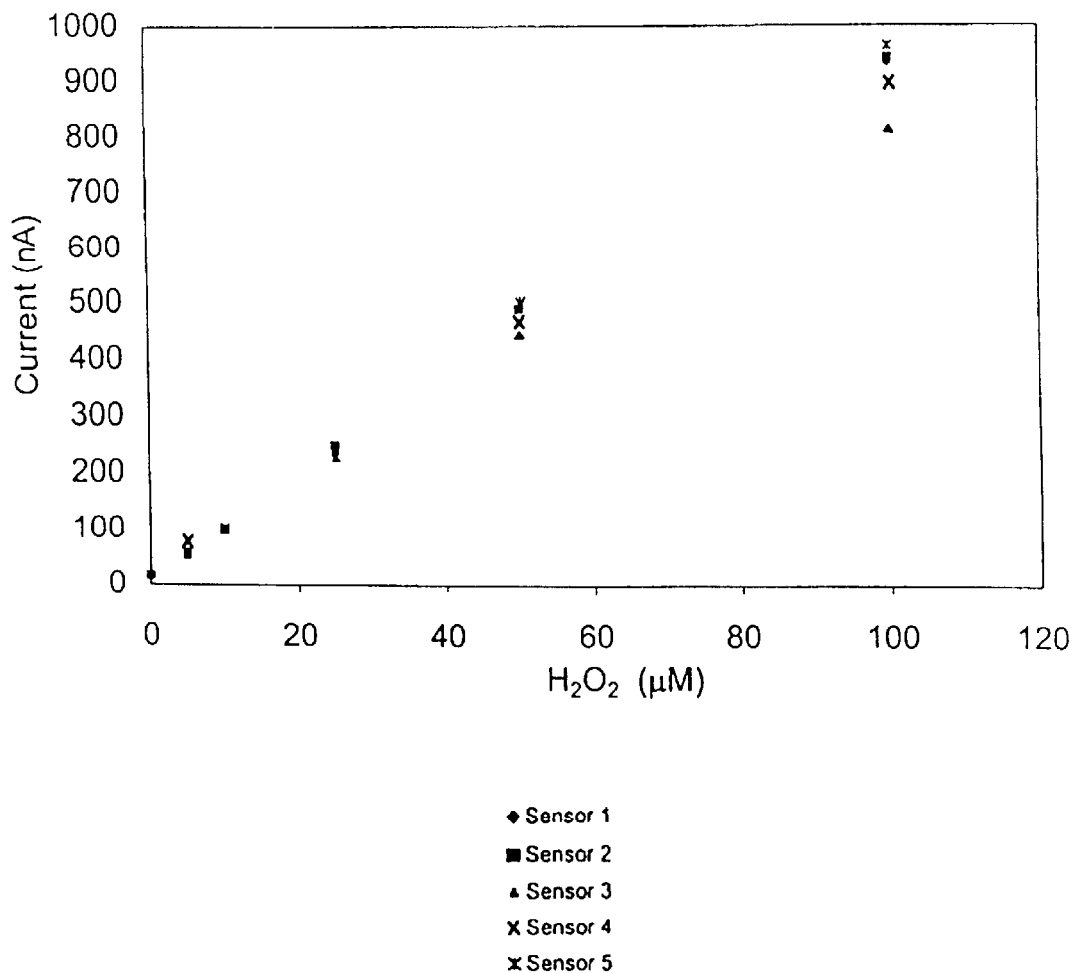
FIG. 4 is a graph showing that signal as a function of concentration of peroxide is linear.

This example demonstrates that current generated from electrodes responsive to hydrogen peroxide is reproducible and linear at low concentrations of hydrogen peroxide. Peroxide is a final product from the ALT enzymatic reaction, as shown in Example 1. Sensors employing carbon working and counter electrodes, and a Ag/AgCl reference electrode were purchased from AndCare (#7101, Research Triangle Park, N.C.). Referring now to FIG. 2, the AndCare sensor 200 comprises a meter-contactable layer 202 and an overcoat layer 204. The sensor 200 further comprises a working electrode 206, a counter electrode 208, and a reference electrode 210 disposed on the meter-contactable layer 202. Running from the electrodes 206, 208, and 210 to electrical contacts 212, 214, and 216 are conductive tracks 218, 220, and 222. The conductive tracks 218, 220, and 222, which are disposed beneath the overcoat layer 204, are shown in phantom. The carbon electrodes were modified to render them sensitive to hydrogen peroxide. A volume of surfactant solution (0.9 microliter, #CF-1075 WENZ, Bioanalytical Systems, West Lafayette, Ind.) was dispensed onto the carbon working electrode (4 mm diameter) by means of a 1 micoliter syringe and the surfactant was allowed to dry for 20 minutes. Next, 0.9 microliter of a peroxidase redox polymer (Peroxidase Redox polymer, #80217, Bioanalytical Systems) was applied over the layer of surfactant and the polymer was allowed to dry overnight under ambient conditions. Electrochemical measurements were carried out on a home-built potentiostat. Five sensors were evaluated at the following hydrogen peroxide concentrations in phosphate buffer (50 mM sodium phosphate pH 7.5, 100 mM NaCl, 1 mM EDTA, 0.05% w/v Kathon CG®): 0, 5, 10, 20, 50, and 100 $\mu$M. Peroxide sample (50 $\mu$L) was dispensed over the electrode area so as to cover the working, reference, and counter electrodes, and a potential of 100 mV was applied for 60 seconds. The current produced at the working electrode was measured every 0.5 second. Current obtained during the last 2.5 seconds of the measurement was averaged and plotted versus peroxide concentration for each sensor in FIG. 4. This example shows that current from low levels of peroxide are reproducible and linear on the AndCare sensor. The AndCare sensor will be shown to have a smooth surface.

Example 3

Figure 5:
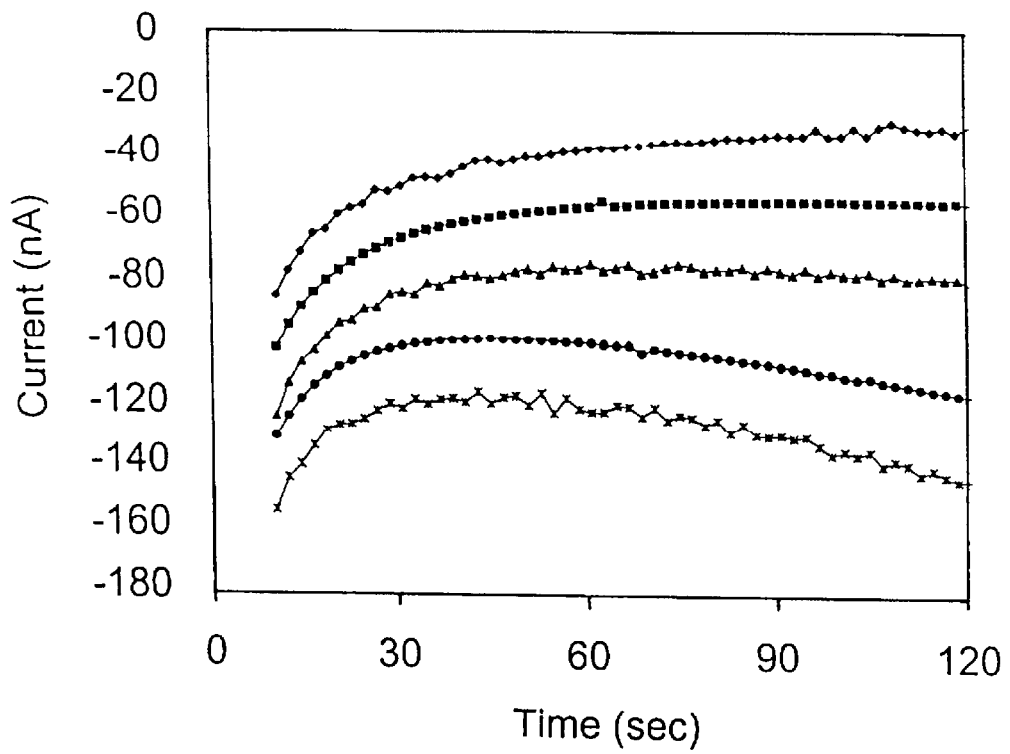
FIG. 5 is a graph showing signal as a function of time for various concentrations of ALT.
Figure 6:
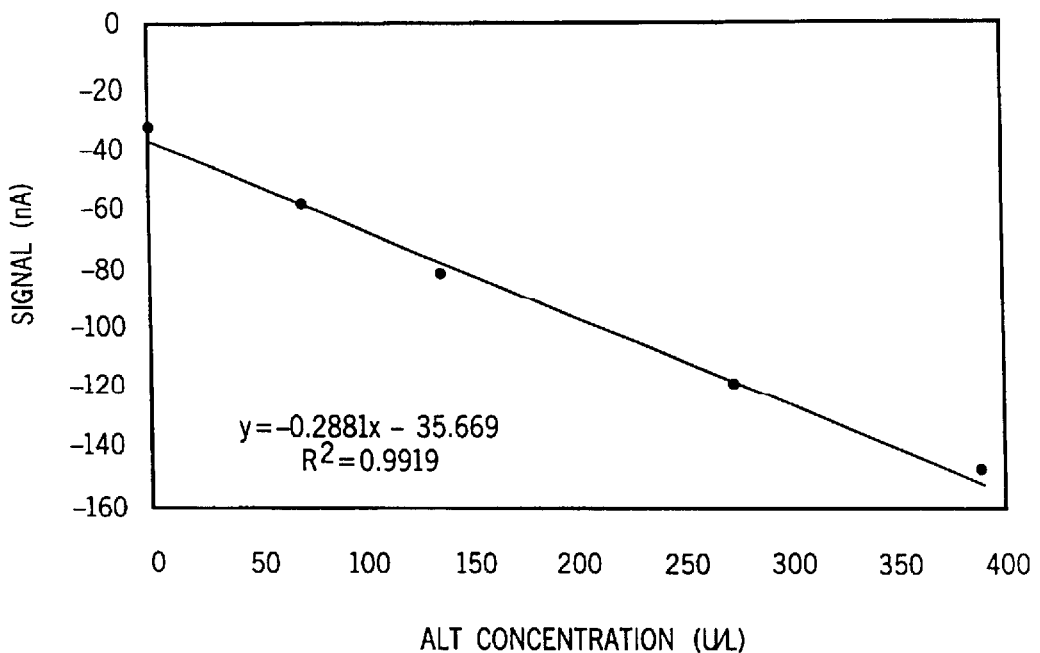
FIG. 6 is a graph showing signal as a function of concentration of ALT.

This example demonstrates the current generated on a pure platinum electrode as a result of the ALT reaction at several concentrations of ALT. A 1.6 mm diameter platinum working electrode (#MF-2013), a platinum wire counter electrode (#MW-1032), and a Ag/AgCl reference electrode (#MF-2063) were purchased from Bioanalytical Systems. The platinum electrode was polished with alumina (#CF-1050, Bioanalytical Systems) to obtain a fresh, smooth surface prior to running the experiment. Electrochemical measurements were carried out on a home-built potentiostat. ALT reagent was prepared by combining the following ingredients: 0.5 M alanine, 10 mM $\alpha$-ketoglutarate, 13 $\mu$M pyridoxal 5'-phosphate, 0.8 U/mL glutamate oxidase, 0.34 mM trehalose, 0.049 % (w/v) bovine serum albumin, 50 mM N-[2 hydroxyethyl]piperazine-N'-[2-ethanesulfonic acid] (hereinafter "HEPES") pH 7.4, 100 mM sodium chloride, 0.05 % (w/v) Kathon CG®. The working, counter, and reference electrodes were introduced into a vial containing 10 mL of ALT reagent. A concentrated stock solution of ALT (#G8255, Sigma, St. Louis, Mo.) was prepared to have an activity of 200 U/mL in HEPES buffer (50 mM HEPES pH 7.4, 100 mM NaCl, 0.05 % w/v Kathon CG®) with 0.1 % w/v bovine serum albumin. Different volumes of the ALT stock solution or HEPES buffer were added to the vial to make the ALT test concentrations listed below. After the ALT stock was added to the vial containing the ALT reagent, the reaction mixture was further mixed. The resulting mixture was incubated at room temperature for 2.5 minutes. A potential of 500 mV was applied to the system and measurements of current were taken every two seconds for two minutes. The above procedure was run a total of five times at ALT concentrations of 0, 69, 134, 271, and 387 U/L. FIG. 5 shows the current transients from the platinum electrode during the two minute read for the different concentrations of ALT. Current (nAmps) was averaged over the last ten seconds for each test run and was plotted against the concentration of ALT (U/L) in the sample. FIG. 6 shows the ALT dose response curve of the smooth platinum electrode. This example shows that ALT can be detected on a smooth platinum electrode.

Example 4

This example demonstrates the ALT dose response curve in human serum using a dried reagent layer and smooth electrodes having redox polymer deposited thereon. The electrodes were prepared as described in Example 2.

Preparation of ALT reagent. Glutamate oxidase (#7804, Yamasa Corporation, Japan) was dissolved in 2 mL of HEPES buffer (50 mM HEPES pH 7.4,100 mM NaCl, 0.05% w/v Kathon CG®). The enzyme was buffer exchanged twice using a 3 mL Slide-A-Lyzer cassette™ (#66425, Pierce, Rockford, Ill.) in HEPES buffer. The glutamate oxidase solution was diluted to 50 U/mL in HEPES buffer, and trehalose was added at a concentration of 0.085 M. ALT reagent was prepared and mixed thoroughly until dissolved. Aliquots of the ALT reagent (125 μL) were dispensed into microfuge tubes. The tubes were placed in a desiccated vacuum chamber, and the reagent was allowed to dry overnight. Aliquots of the glutamate oxidase solution (10 μL) were dispensed into the microfuge tubes containing the dried ALT reagent. The tubes were placed in the desiccated vacuum chamber to dry the enzyme solution. Final concentrations of components of the ALT reagent when re-dissolved with sample were: 0.5 M alanine, 10 mM α-ketoglutarate, 13 μM pyridoxal 5'-phosphate, 2 U/mL glutamate oxidase, 3.4 mM trehalose, 25 mM HEPES pH 7.4, 50 mM sodium chloride, 0.025% w/v Kathon CG®.

Figure 7:
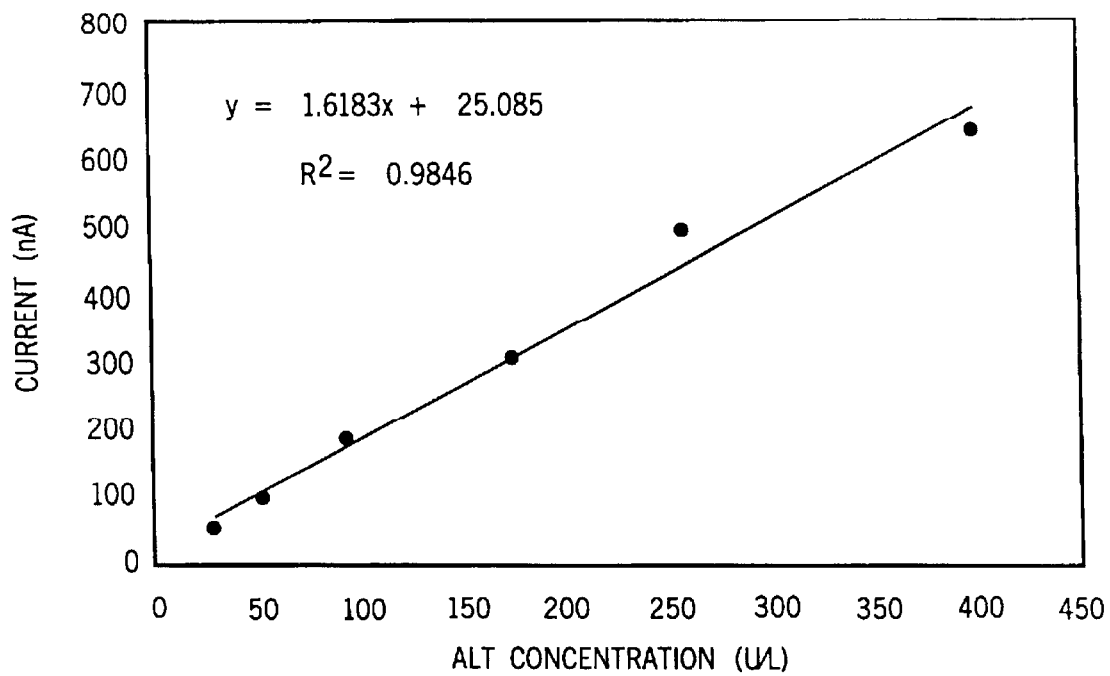
FIG. 7 is a graph showing signal as a function of concentration of ALT in serum.

Experimental Procedure. All reagents and human serum were equilibrated to room temperature before the experiment was run. An ALT stock solution was prepared to 10 U/mL in HEPES buffer with 0.1% w/v bovine serum albumin. The ALT stock solution was spiked into one mL aliquots of human serum to make final ALT concentrations of 93, 174, 259, and 401 U/L. Endogenous serum ALT was 28 U/L. The samples were measured for ALT concentration in replicate runs using SGOT (ALT) testpacks (#1423, Abbott Laboratories, Abbott Park, Ill.) on an Abbott VISION™ analyzer. ALT serum sample (250 μL) was added to a microfuge tube containing dried ALT reagent. The tube was lightly agitated for one minute. The reaction was allowed to proceed in the microfuge tube for a total of 140 seconds, at which time 50 μL of the sample-reaction mixture was dispensed over the electrode area of the redox polymer electrode covering the working, reference, and counter electrodes. After a total incubation period of 150 seconds, a potential of 100 mV was applied to the electrode, and the current was monitored at two second intervals for two minutes. Two experimental runs for each of the five different ALT concentrations were carried out. Current generated over the last ten seconds of each run was averaged. Currents from the replicate runs were averaged. In FIG. 7, the average current results obtained for each ALT concentration were plotted against the average VISION™ ALT results. It can be seen that the ALT dose response was linear in the range examined (28 to 401 U/L) using dried reagents and a smooth electrode.

Example 5

Figure 8:
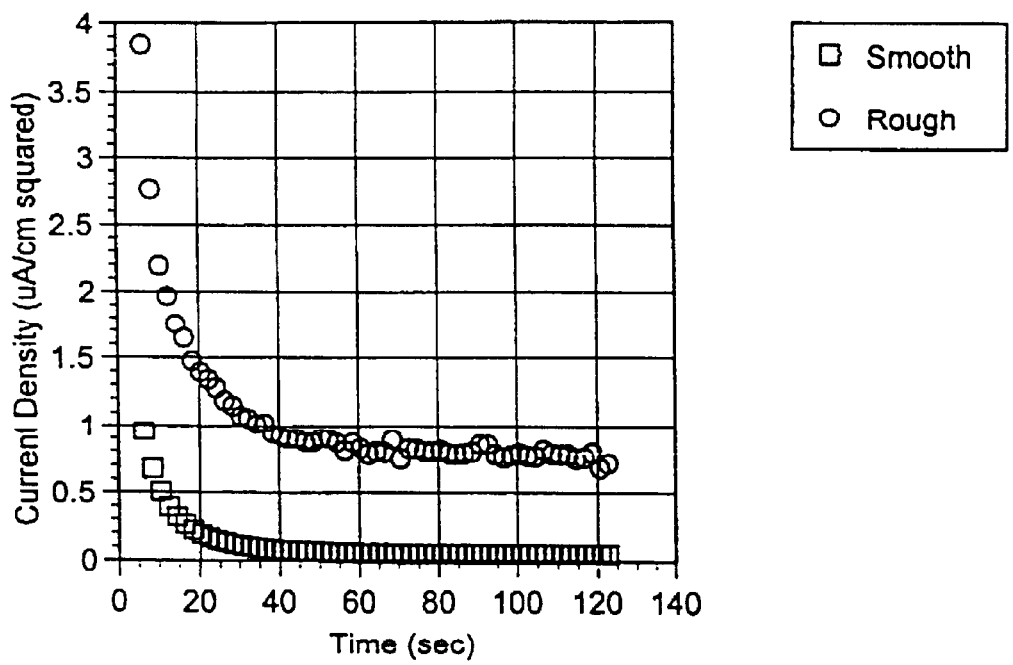
FIG. 8 is a graph showing background signals as a function of roughness of the surface of the working electrode.

The purpose of this example is to demonstrate the effect that the surface roughness of the electrode has on the background current of an ALT assay. Background current is the current that is generated by the electrode in the absence of analyte. One source of the background current is double layer charging current. Electrodes having relatively rougher surfaces will have more double layer charging current than electrodes having relatively smoother surfaces. An AndCare carbon electrode (relatively smooth surface) and a printed carbon electrode fabricated in-house (relatively rough surface) were used in this experiment. The in-house electrode was prepared according to U.S. Pat. No. 5,755,953. Surface roughness measurements were taken of representative smooth and rough electrodes by means of a Dektak[3] surface profile measuring system (Veeco Instruments, Santa Barbara, Calif.). The arithmetic average roughness, Ra, was 6779 Angstroms for the AndCare electrode and 54700 Angstroms for the in-house electrode. The AndCare and in-house electrodes were modified by dispensing a surfactant solution and peroxidase redox polymer onto the working electrodes, as described in Example 2. The volumes dispensed were 0.9 μL and 2.0 μL for the AndCare and in-house electrodes, respectively. Current measurements were made at 100 mV in HEPES buffer (50 mM HEPES pH 7.4,100 mM NaCl, 1 mM sodium EDTA). The current was monitored at two second intervals for two minutes. A comparison of the current density for the smooth and rough electrodes is shown in FIG. 8. As can be seen, the in-house electrode had a significantly higher background current than did the AndCare electrode. Additionally, there was more variation in the current from the in-house electrode. The accurate measurement of small ALT signals will clearly be more difficult on the in-house electrode because of the larger background current, as was demonstrated in Example 6.

Example 6

The purpose of this example is to demonstrate that the working electrode needs to be sufficiently smooth to accurately detect small ALT currents. AndCare carbon electrodes (relatively smooth surface) and in-house fabricated printed carbon electrodes (relatively rough surface) were coated with redox polymer as described in Example 5. Electrode areas of the AndCare and in-house electrodes were 0.1257 $cm^2$ and 0.0452 $cm^2$, respectively. Background currents were measured for each type of electrode with HEPES buffer (50 mM HEPES pH 7.4, 100 mM NaCl, 1 mM EDTA) as described in Example 5. Table I lists the surface roughness and current background results of each electrode.

TABLE I

| Electrode | Surface Roughness, Ra (Angstroms) | Background Current Density (nA/cm$^2$) | Standard Deviation (nA/cm$^2$) | No. of sensors run |
|---|---|---|---|---|
| Smooth | 6779 | 41.4 | 6.2 | 5 |
| Rough | 54700 | 673.5 | 62.5 | 9 |

ALT reagent was prepared with HEPES buffer as described in Example 4. An ALT sample was prepared in HEPES buffer with bovine serum albumin (0.1% w/v). The concentration of ALT in the sample was about 28 U/L, which is a clinically normal level. ALT measurements were made on the electrodes as described in Example 4. Current outputs corrected for electrode area for the ALT sample are shown in Table II.

TABLE II

| Electrode | Average Current Density (nA/cm²) | Coefficient of variation | No. of sensors run |
|---|---|---|---|
| Smooth | 1604 | 5.0 | 5 |
| Rough | 1476 | 10.3 | 12 |

The background currents corrected for area were more than 16 times higher for the rough electrodes than for the smooth electrodes (Table I). The level of background current for the smooth electrodes was less than 3% of that of the ALT current (Table II). The level of background current for the rough electrodes was 45% of that of the ALT current. Accurately measuring the small ALT currents with the rough electrodes is difficult because the background current is so large relative to the ALT current. The variation of the background signal for the rough electrodes in this example would cause up to a 4.2% change in the total current measurement of the ALT sample, leading to a substantial error in the ALT determination. For the smooth electrodes, the background signal variation would only cause up to a 0.4% change in the total current measurement of the ALT sample. Coefficient of variation results for the ALT currents on the rough electrodes (10.3% CV) was 106% larger than that on the smooth electrodes (5% CV). Thus, it can be seen that a multiple-layer element having a smooth working electrode produces a more accurate result than does a multiple-layer element having a working electrode with a rough surface.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A biosensor for determining the concentration of an analyte in a sample of whole blood, said biosensor consisting essentially of:
   (a) a base layer;
   (b) a detecting layer comprising a reference electrode and a working electrode, the surface of the electrically conductive portion of the working electrode having a surface roughness not exceeding 10,000 Angstroms, wherein said surface roughness allows the determination of the concentration of an analyte present at a concentration of less than I mM in a sample of whole blood to be made;
   (c) a layer overlying said electrodes, said layer comprising at least one dried reagent; and
   (d) an anticoagulant disposed in such a location that it will prevent the sample of whole blood from coagulating during the determination, said biosensor further including a liquid-impermeable covering layer enclosing said electrodes to reduce evaporation of said sample of whole blood.

2. The biosensor of claim 1, wherein said working electrode is made of a material selected from the group consisting of carbon, platinum, gold, palladium, silver chloride, and silver.

3. The biosensor of claim 1, wherein said biosensor further includes a fluid-transporting layer.

4. The biosensor of claim 3, wherein said fluid-transporting layer comprises a hydrophilic mesh.

5. The biosensor of claim 1, wherein said working electrode further includes a redox polymer.

6. The biosensor of claim 1, wherein said working electrode further includes a peroxidase enzyme and carbon.

7. The biosensor of claim 1, wherein said working electrode does not dissolve upon exposure to fluid.

8. The biosensor of claim 1, wherein said fluid is whole blood and said analyte is ALT.

9. A method for determining the concentration of an analyte in a sample of whole blood, said method comprising the steps of:
   (1) providing a biosensor consisting essentially of:
      (a) a base layer;
      (b) a detecting layer comprising a reference electrode and a working electrode, the surface of the electrically conductive portion of the working electrode having a surface roughness not exceeding 10,000 Angstroms, wherein said surface roughness allows the determination of the concentration of an analyte present at a concentration of less than 1 mM in a sample of whole blood to be made;
      (c) a layer overlying said electrodes, said layer comprising at least one dried reagent; and
      (d) an anticoagulant disposed in such a location that it will prevent the sample of whole blood from coagulating during the determination, said biosensor further including a liquid-impermeable covering layer enclosing said electrodes to reduce evaporation of said sample of whole blood;
   (2) introducing a sample of whole blood to said biosensor;
   (3) allowing said sample of whole blood to dissolve said at least one dried reagent;
   (4) allowing a chemical reaction to occur at said detecting layer; and
   (5) reading the output of said chemical reaction, whereby the concentration of said analyte is determined.

10. The method of claim 9, wherein said working electrode is made of a material selected from the group consisting of carbon, platinum, gold, palladium, silver chloride, and silver.

11. The method of claim 9, wherein said biosensor further is includes a fluid-transporting layer.

12. The method of claim 11, wherein said fluid-transporting layer comprises a hydrophilic mesh.

13. The method of claim 9, wherein said working electrode further includes a redox polymer.

14. The method of claim 9, wherein said working electrode further includes a peroxidase enzyme and carbon.

15. The method of claim 9, wherein said working electrode does not dissolve upon exposure to fluid.

16. The method of claim 9, wherein said fluid is whole blood and said analyte is ALT.

* * * * *

UNITED STATES PATENT AND TRADEMARK OFFICE
CERTIFICATE OF CORRECTION

PATENT NO. : 6,565,738 B1  Page 1 of 1
DATED : May 20, 2003
INVENTOR(S) : Timothy P. Henning et al.

It is certified that error appears in the above-identified patent and that said Letters Patent is hereby corrected as shown below:

Column 24,
Line 49, delete the word -- is --.

Signed and Sealed this

Sixth Day of July, 2004

JON W. DUDAS
*Acting Director of the United States Patent and Trademark Office*